US00PP35926P2

(12) United States Plant Patent
Arts

(10) Patent No.: US PP35,926 P2
(45) Date of Patent: Jul. 2, 2024

(54) ***HYDRANGEA* PLANT NAMED 'H223904'**

(50) Latin Name: *Hydrangea macrophylla*
Varietal Denomination: H223904

(71) Applicant: HYDRANGEA BREEDERS ASSOCIATION B.V., De Kwakel (NL)

(72) Inventor: Niels Arts, Aalsmeer (NL)

(73) Assignee: HYDRANGEA BREEDERS ASSOCIATION B.V., De Kwakel (NL)

( * ) Notice: Subject to any disclaimer, the term of this patent is extended or adjusted under 35 U.S.C. 154(b) by 0 days.

(21) Appl. No.: 18/206,261

(22) Filed: Jun. 6, 2023

(51) Int. Cl.
*A01H 5/02* (2018.01)
*A01H 6/48* (2018.01)

(52) U.S. Cl.
USPC ..... Plt./250
CPC ..... *A01H 6/48* (2018.05); *A01H 5/02* (2013.01)

(58) Field of Classification Search
USPC ..... Plt./250
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Hydrangea* plant named 'H223904', characterized by its relatively compact, upright and uniformly mounded plant habit; vigorous growth habit and rapid growth rate; freely branching habit with strong, thick and sturdy stems; freely and uniformly flowering habit; mophead-type inflorescences with numerous sterile flowers that are white in color; and good postproduction longevity.

2 Drawing Sheets

Figure 1:
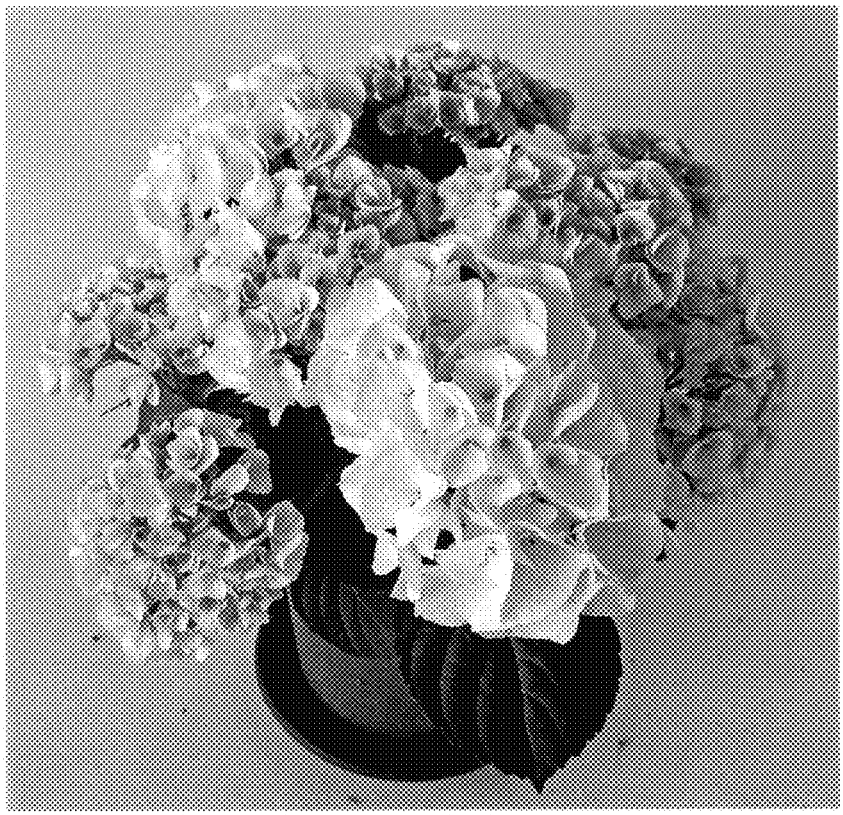

Botanical designation: *Hydrangea macrophylla.*
Cultivar denomination: 'H223904'.

CLOSELY-RELATED APPLICATION(S)

An European Community Plant Breeder's Rights application for the instant plant was filed by the Applicant/Assignee, *Hydrangea* Breeders Association B.V. of De Kwakel, The Netherlands on Mar. 9, 2023, application number 2023/0593. Foreign priority is not claimed to this application.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'H223904'.

The new *Hydrangea* plant is a product of a planned breeding program conducted by the Inventor in De Kwakel, The Netherlands and Lengerich, Germany. The objective of the breeding program was to create new strong and freely-branching *Hydrangea* plants with strong sturdy stems, uniform flowering habit, large inflorescences with numerous showy sterile flowers, attractive sterile flower color and good postproduction longevity.

The new *Hydrangea* plant originated from a cross-pollination made by the Inventor during the spring of 2017 in De Kwakel, The Netherlands, of *Hydrangea macrophylla* 'Agrihydrazeventien', disclosed in U.S. Plant Pat. No. 26,453, as the female, or seed, parent with a proprietary selection of *Hydrangea macrophylla* identified as code number 211259-002, not patented, as the male, or pollen, parent. The new *Hydrangea* plant was discovered and selected by the Inventor as a single flowering plant from within the progeny of the stated cross-pollination in a controlled greenhouse environment in Lengerich, Germany during the spring of 2019.

Asexual reproduction of the new *Hydrangea* plant by vegetative tip cuttings in a controlled environment in De Kwakel, The Netherlands since the summer of 2019 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H223904'. These characteristics in combination distinguish 'H223904' as a new and distinct *Hydrangea* plant:

1. Relatively compact, upright and uniformly mounded plant habit.
2. Vigorous growth habit and rapid growth rate.
3. Freely branching habit with strong, thick and sturdy stems.
4. Freely and uniformly flowering habit.
5. Mophead-type inflorescences with numerous sterile flowers that are white in color.
6. Good postproduction longevity.

Plants of the new *Hydrangea* can be compared to plants of the female parent, 'Agrihydrazeventien'. Plants of the new *Hydrangea* differ primarily from plants of 'Agrihydrazeventien' in growth habit as plants of the new *Hydrangea* are more vigorous than plants of 'Agrihydrazeventien'.

In addition, plants of the new *Hydrangea* have better post-production longevity than plants of 'Agrihydrazeventien'.

Plants of the new *Hydrangea* can be compared to plants of the male parent selection. Plants of the new *Hydrangea* differ primarily from plants of the male parent selection in sterile flower color as sterile flowers of plants of the new *Hydrangea* are more white than and not as yellowish white in color than sterile flowers of plants of the male parent selection.

Plants of the new *Hydrangea* can be compared to plants of the *Hydrangea macrophylla* 'Agrihydraveertien', disclosed in U.S. Plant Pat. No. 23,802. In side-by-side comparisons, plants of the new *Hydrangea* differ primarily from plants of 'Agrihydraveertien' in the following characteristics:

1. Plants of the new *Hydrangea* are shorter and broader than plants of 'Agrihydraveertien'.
2. Plants of the new *Hydrangea* have darker green-colored leaves than plants of 'Agrihydraveertien'.
3. Sterile flowers of plants of the new *Hydrangea* are more white than and not as yellowish white as sterile flowers of plants of 'Agrihydraveertien'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a top perspective view of a typical flowering plant of 'H223904'.

Figure 2:
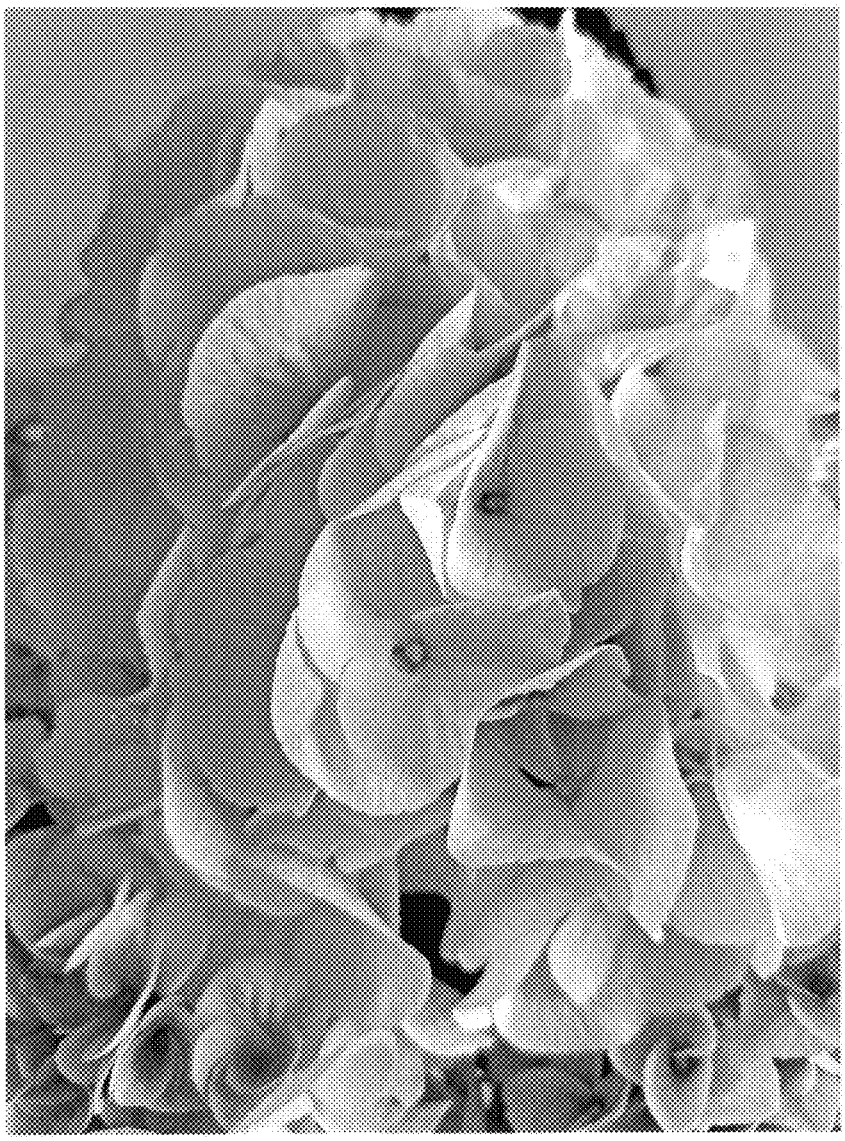

The photograph on the second sheet (FIG. 2) is a close-up view of a typical inflorescence of 'H223904'.

DETAILED BOTANICAL DESCRIPTION

Plants used in the aforementioned photographs and in the following description were grown during the summer in 17-cm containers in a glass-covered greenhouse in Lengerich, Germany and under cultural practices typical of commercial *Hydrangea* production. During the production of the plants, day and night temperatures averaged 17C. Plants of the new *Hydrangea* were 14 months old when the photographs and description were taken. Plants of the new *Hydrangea* are typically not treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'H223904'.

Parentage:

*Female, or seed, parent.*—*Hydrangea macrophylla* 'Agrihydrazeventien', disclosed in U.S. Plant Pat. No. 26,453.

*Male, or pollen, parent.*—Proprietary selection of *Hydrangea macrophylla* identified as code number 211259-002, not patented.

Propagation:

*Type cutting.*—By vegetative tip cuttings.

*Time to initiate roots, summer.*—About two weeks at temperatures about 23C.

*Time to initiate roots, winter.*—About 18 days at temperatures about 20C.

*Time to produce a rooted young plant, summer.*—About four weeks at temperatures about 23C.

*Time to produce a rooted young plant, winter.*—About five weeks at temperatures about 20C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Relatively compact, upright and uniformly mounded plant habit; strong and sturdy stems; rapid growth rate and vigorous growth habit.

*Plant height.*—About 20 cm to 22 cm.

*Plant diameter or area of spread.*—About 40 cm.

Lateral branch description:

*Branching habit.*—Freely branching habit; when pinched, about eight lateral branches develop per plant.

*Length.*—About 10 cm.

*Diameter.*—About 8 mm.

*Internode length.*—About 3 cm.

*Texture.*—Smooth, glabrous; fully developed, woody.

*Aspect.*—Upright to slightly outwardly.

*Strength.*—Strong, sturdy.

*Color.*—When developing: Close to 144A. Fully developed: Close to 177C.

Leaf description:

*Arrangement.*—Opposite, simple.

*Length.*—About 10 cm.

*Width.*—About 8 cm to 9 cm.

*Shape.*—Ovate.

*Apex.*—Acute.

*Base.*—Obtuse.

*Margin.*—Dentate to serrate.

*Texture, upper surface.*—Smooth, glabrous.

*Texture, lower surface.*—Rugose, glabrous.

*Venation pattern.*—Pinnate.

*Color.*—Developing leaves, upper surface: Close to 136A. Developing leaves, lower surface: Close to 137B. Fully expanded leaves, upper surface: Close to 136A; venation, close to 146C. Fully expanded leaves, lower surface: Close to 137B; venation, close to 146C.

*Petioles.*—Length: About 2 cm. Diameter: About 4 mm. Texture, upper and lower surfaces: Smooth, glabrous. Color, upper and lower surfaces: Close to 146C.

Flower description:

*Flower type and habit.*—Small and inconspicuous fertile flowers and showy sterile flowers arranged on mophead-type terminal panicles; panicles upright and flattened globular in shape; fertile and sterile flowers face outwardly depending on their position in the inflorescence.

*Fragrance.*—None detected.

*Time to flowering.*—Plants begin flowering about eight weeks after cold treatment.

*Flower longevity.*—Fertile flowers last about four weeks on the plant, fertile flowers not persistent; sterile flowers last about four months on the plant, sterile flowers persistent.

*Quantity of flowers.*—Freely flowering habit; about 20 fertile flowers and about 80 to 100 sterile flowers per panicle.

*Panicle height.*—About 8 cm.

*Panicle diameter.*—About 13 cm to 16 cm.

*Fertile flower buds.*—Length: About 3 mm to 4 mm. Diameter: About 3 mm to 4 mm. Shape: Spherical. Color: Close to 145B.

*Sterile flower buds.*—Length: About 1 cm. Diameter: About 1 cm. Shape: Spherical. Color: Close to 145A.

*Fertile flower diameter.*—About 3 mm to 4 mm.

*Fertile flower depth* (*height*).—About 5 mm.

*Sterile flower diameter.*—About 4 cm to 4.5 cm.

*Sterile flower depth* (*height*).—About 1 cm.

*Petals, fertile flowers.*—Quantity and arrangement: About five in a single whorl. Length: About 3 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 155A. Fully opened, upper and lower surfaces: Close to 155A; color does not change with subsequent development.

*Petals, sterile flowers.*—Quantity and arrangement: About four in a single whorl. Length: About 3 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 145D. Fully opened, upper and lower surfaces: Close to NN155A; color does not change with subsequent development.

*Sepals, fertile flowers.*—Quantity and arrangement: About five in a single whorl. Length: About 1 mm to 2 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 145C. Fully opened, upper and lower surfaces: Close to 145C; color does not change with subsequent development.

*Sepals, sterile flowers.*—Quantity and arrangement: About four in a single whorl. Length: About 2 cm to 2.5 cm. Width: About 3 cm to 3.5 cm. Shape: Deltoid. Apex: Obtuse. Base: Obtuse. Margin: Entire. Texture, upper and lower surfaces: Smooth, glabrous. Color: When opening, upper and lower surfaces: Close to 145D. Fully opened, upper and lower surfaces: Close to NN155B; color becoming closer to 157B.

*Pedicels, fertile flowers.*—Length: About 3 mm to 5 mm. Diameter: About 1 mm. Strength: Strong. Aspect: Mostly upright. Texture: Smooth, glabrous. Color: Close to 145D.

*Pedicels, sterile flowers.*—Length: About 2.5 cm. Diameter: About 2 mm. Strength: Strong. Aspect: About 45 degrees from vertical. Texture: Smooth, glabrous. Color: Close to 155A.

*Reproductive organs, fertile flowers.*—Stamens: Quantity per flower: About eight. Filament length: About 1 mm. Filament color: Close to 155A. Anther length: About 2 mm. Anther shape: Round. Anther color: Close to 155A. Pollen amount: Moderate. Pollen color: Close to 155A. Pistils: Pistil quantity per flower: One. Pistil length: About 2 mm. Stigma shape: Three-lobed. Stigma color: Close to 145C. Style length: About 2 mm. Style color: Close to 145C. Ovary color: Close to 145C.

*Reproductive organs, sterile flowers.*—Stamens: Quantity per flower: About six. Filament length: About 2 mm. Filament color: Close to 145D. Anther length: About 1 mm to 2 mm. Anther shape: Round. Anther color: Close to 145D. Pollen amount: Moderate. Pollen color: Close to 155A. Pistils: Pistil quantity per flower: One. Pistil length: About 1 mm to 2 mm. Stigma shape: Two-lobed. Stigma color: Close to 145D. Style length: About 1 mm to 2 mm. Style color: Close to 145D. Ovary color: Close to 145D.

*Seeds, only produced by fertile flowers.*—Quantity per fertile flower: About 20 to 30. Length: About 1 mm. Diameter: About 0.2 mm. Color: Close to 200C.

Pathogen & pest resistance: To date, plants of the new *Hydrangea* grown under commercial production conditions have not been observed to be resistant to pathogens and pests common to *Hydrangea* plants.

Garden performance: Plants of the new *Hydrangea* have been shown to have good garden performance and to be tolerant to temperatures ranging from about 3C to about 38C.

It is claimed:

1. A new and distinct *Hydrangea* plant named 'H223904' as illustrated and described herein.

* * * * *